(12) United States Patent
Gudeman et al.

(10) Patent No.: US 10,136,941 B2
(45) Date of Patent: Nov. 27, 2018

(54) SURGICAL INSTRUMENT AND METHOD OF CREATING THE SAME

(71) Applicants: Matthew S. Gudeman, Buffalo Grove, IL (US); Matthew D Lindberg, Buffalo Grove, IL (US); Mateusz Latawiec, Buffalo Grove, IL (US)

(72) Inventors: Matthew S. Gudeman, Buffalo Grove, IL (US); Matthew D Lindberg, Buffalo Grove, IL (US); Mateusz Latawiec, Buffalo Grove, IL (US)

(73) Assignee: JSTONE INC., Mundelien, IL (US)

( * ) Notice: Subject to any disclaimer, the term of this patent is extended or adjusted under 35 U.S.C. 154(b) by 477 days.

(21) Appl. No.: 14/931,987

(22) Filed: Nov. 4, 2015

(65) Prior Publication Data

US 2017/0119458 A1    May 4, 2017

(51) Int. Cl.
*A61B 18/14* (2006.01)
*A61B 18/00* (2006.01)

(52) U.S. Cl.
CPC ..... *A61B 18/1445* (2013.01); *A61B 2018/00083* (2013.01); *A61B 2018/146* (2013.01)

(58) Field of Classification Search
CPC ............ A61B 18/1442; A61B 18/1445; A61B 2018/146; A61B 2018/00083; A61B 2018/1415; A61B 2018/00077; A61B 17/29; A61B 17/282; A61B 2017/2929; A61B 2017/2948
See application file for complete search history.

(56) References Cited

U.S. PATENT DOCUMENTS

| | | | | |
|---|---|---|---|---|
| 5,352,223 A | * | 10/1994 | McBrayer | A61B 17/2909 606/205 |
| 6,312,430 B1 | * | 11/2001 | Wilson | A61B 18/1445 606/170 |
| 7,879,035 B2 | * | 2/2011 | Garrison | A61B 18/1445 606/45 |
| 8,235,992 B2 | * | 8/2012 | Guerra | A61B 18/1445 606/205 |
| 2007/0078456 A1 | * | 4/2007 | Dumbauld | A61B 18/1445 606/42 |
| 2009/0088750 A1 | * | 4/2009 | Hushka | A61B 18/1445 606/51 |
| 2012/0010611 A1 | * | 1/2012 | Krom | A61B 18/1445 606/41 |

* cited by examiner

*Primary Examiner* — Michael Peffley
(74) *Attorney, Agent, or Firm* — Justin Lampel

(57) ABSTRACT

A surgical instrument is provided, namely surgical scissors. The surgical instrument has liquid-tight heat-shrunk protective covering located at the business end of the surgical instrument which prevents contamination and damage to moving parts of the instrument which otherwise typically occurs between an extended tube portion of the surgical instrument and a head portion of the surgical instrument. Further, the liquid-tight heat shrunk protective covering provides electrical insulation all the way to the distal tip of a clevis of the surgical instrument by use of a rubber (for example silicone) seal. The surgical instrument has a first blade and a second blade secured to the clevis. The first blade and second blade both have a triangular-shaped back end which allows the blades to fully extend without the back ends extending outside of the instrument.

17 Claims, 9 Drawing Sheets

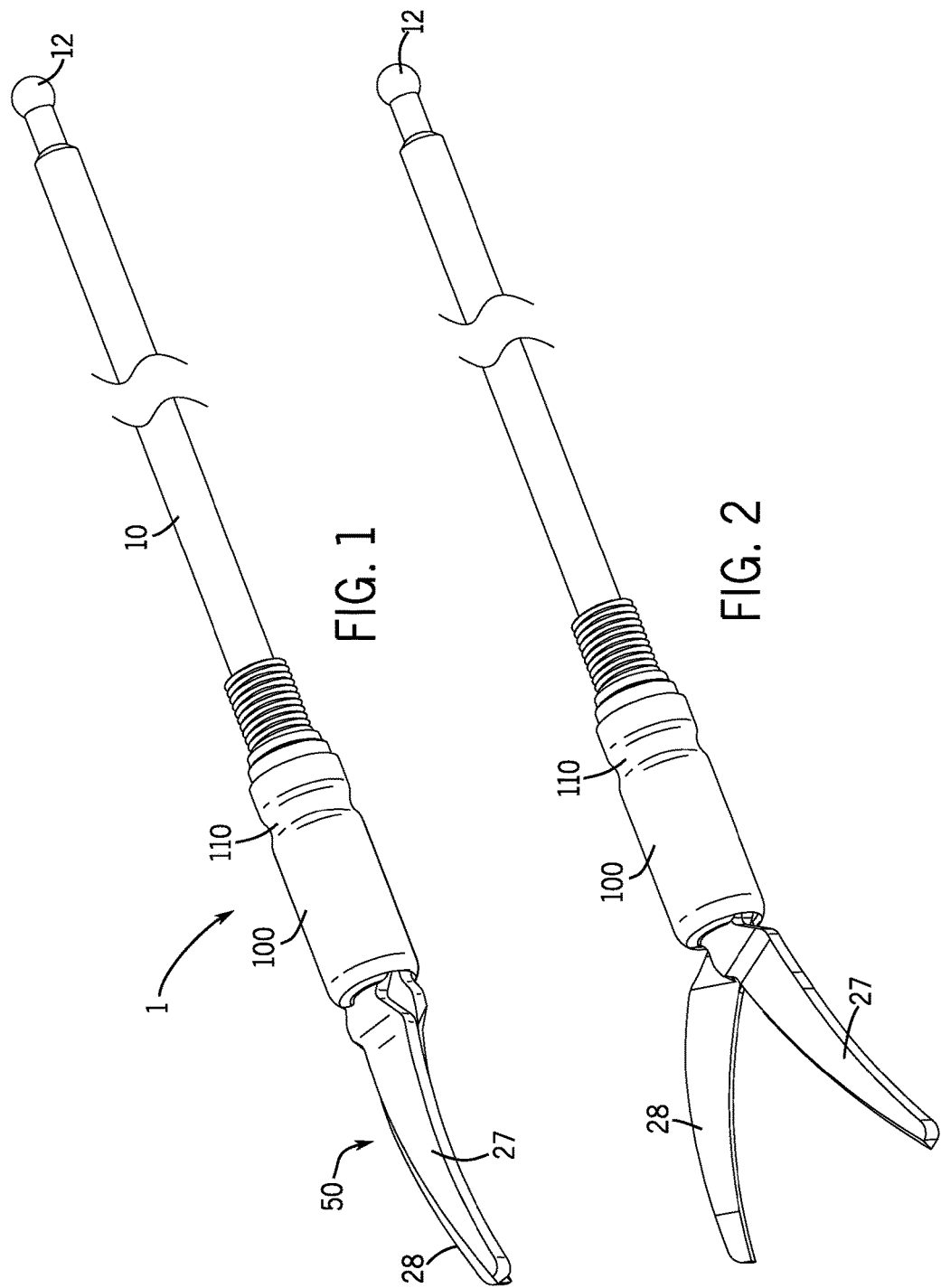

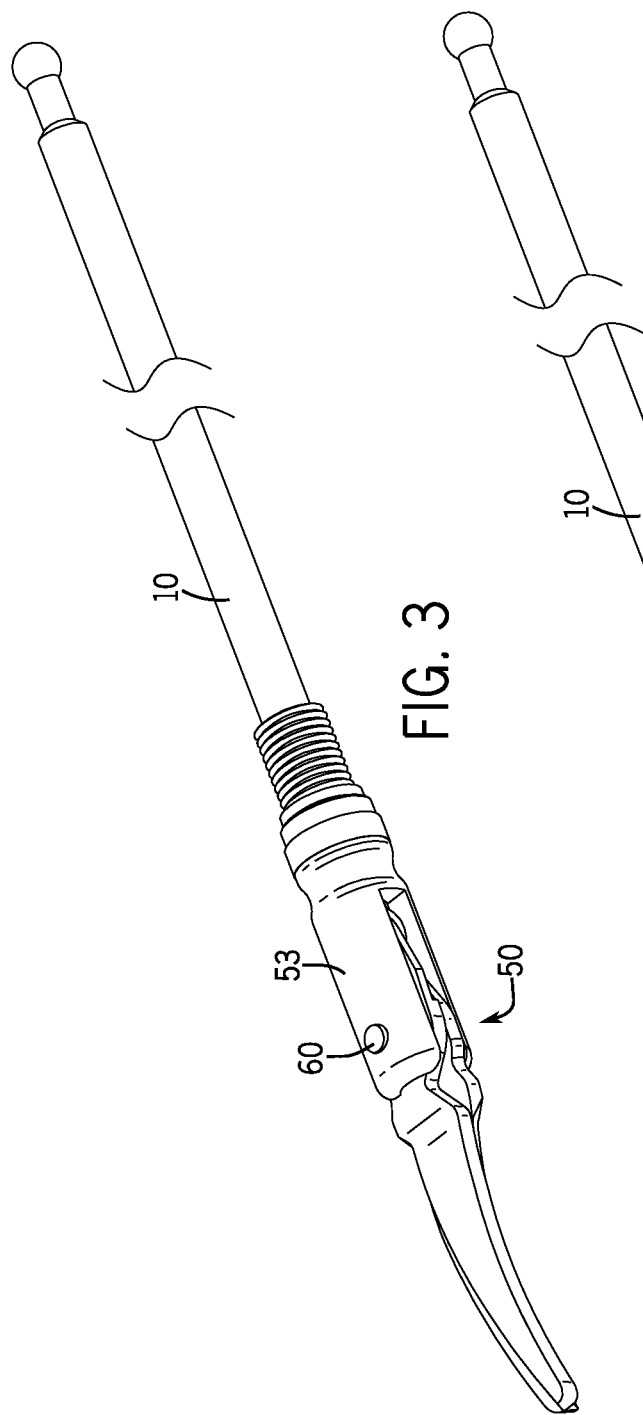

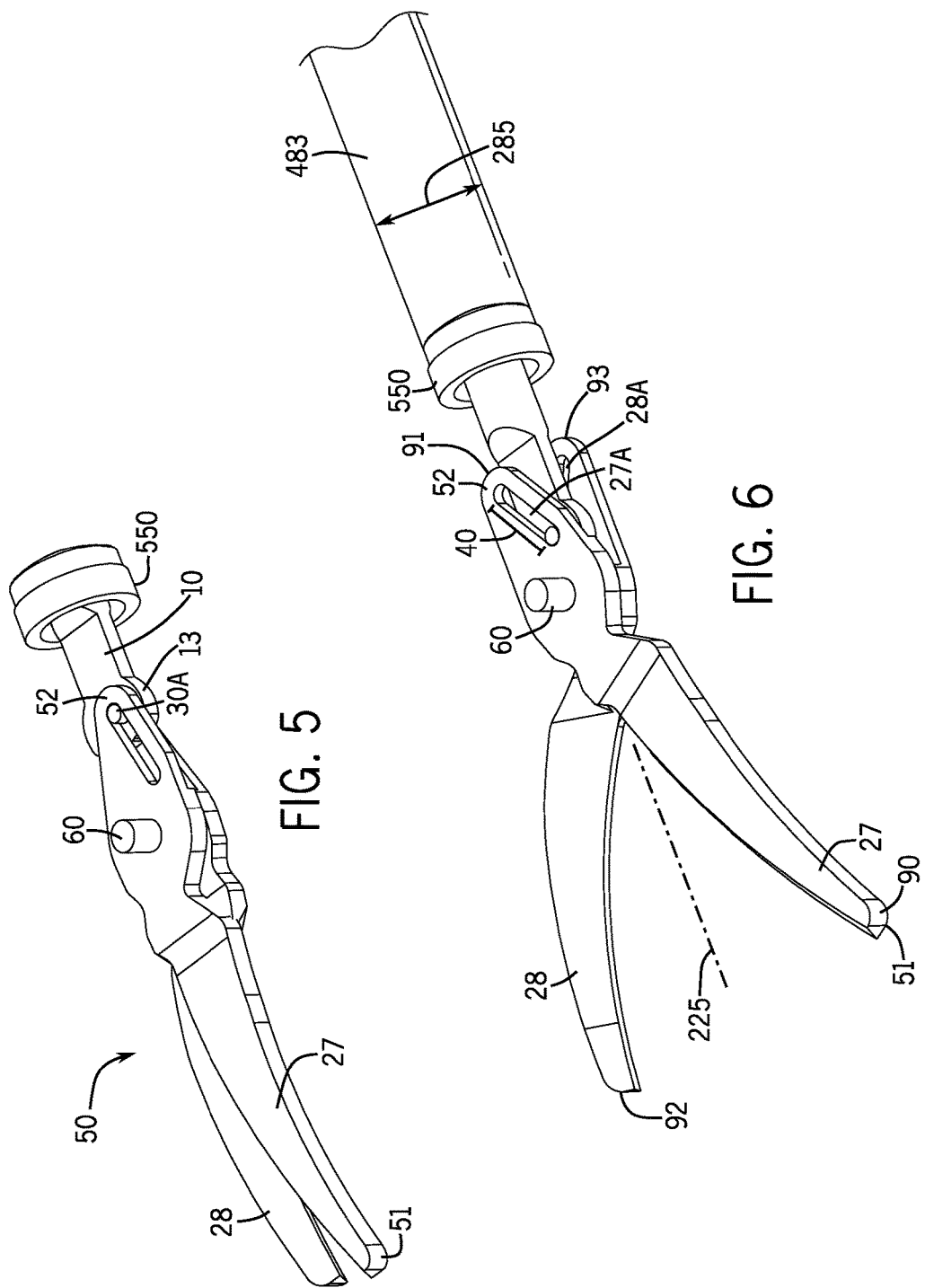

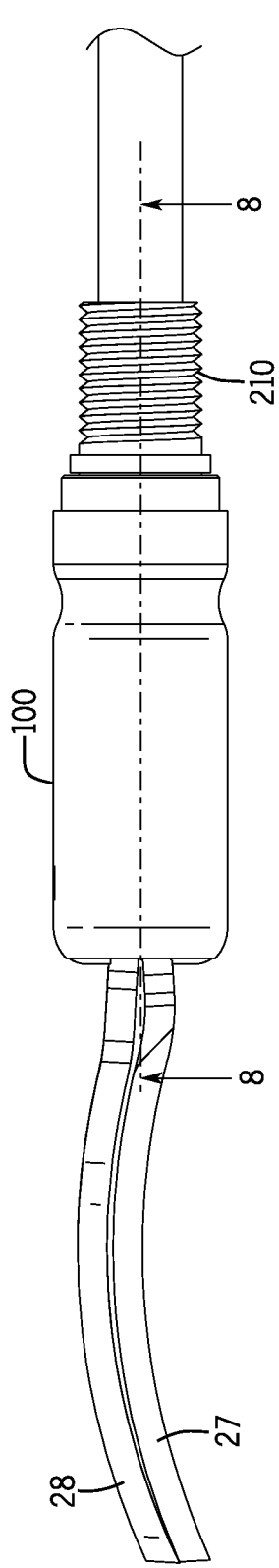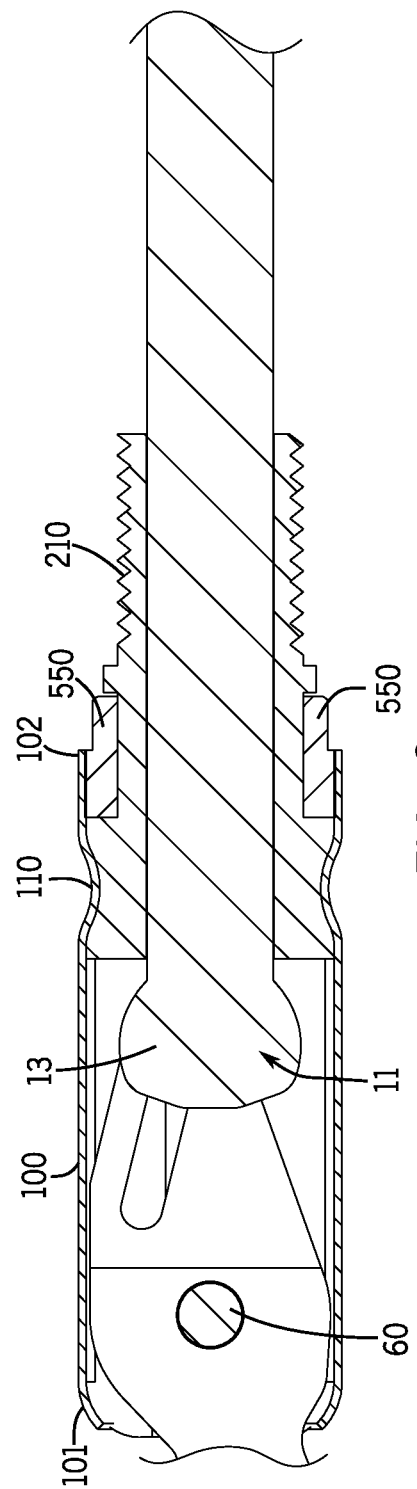

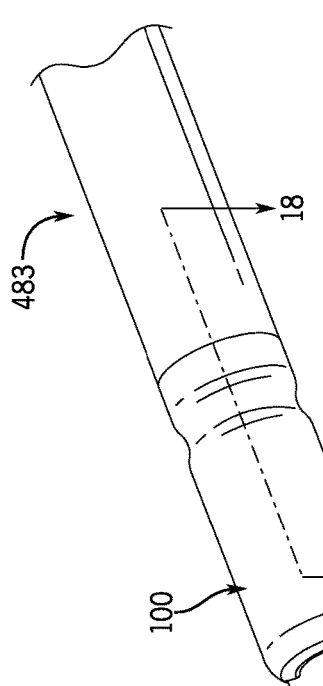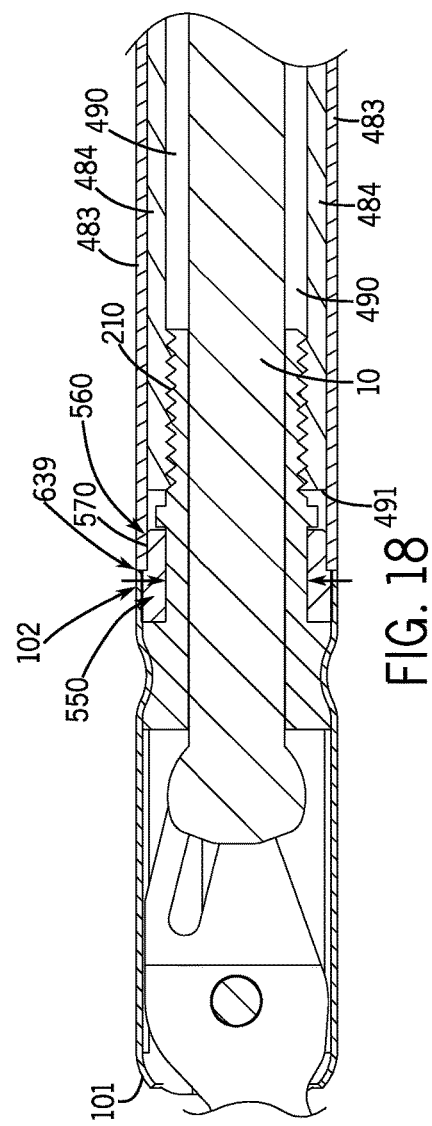

SURGICAL INSTRUMENT AND METHOD OF CREATING THE SAME

BACKGROUND OF THE INVENTION

A surgical instrument is provided, namely surgical scissors. The surgical instrument has liquid-tight heat-shrunk protective covering located at the business end of the surgical instrument which prevents contamination and damage to moving parts of the instrument which otherwise typically occurs between an extended tube portion of the surgical instrument and a head portion of the surgical instrument. Further, the liquid-tight heat-shrunk protective covering provides electrical insulation all the way to the distal tip of a clevis of the surgical instrument by use of a rubber (for example silicone) seal. The surgical instrument has a first blade and a second blade secured to the clevis. The first blade and second blade both have a triangular-shaped back end which allows the blades to fully extend and operate without the triangular-shaped back end of the first and second blade extending beyond the diameter of the clevis or tube of the surgical instrument.

Numerous surgical instruments which utilize a clevis have been invented in the past. For example, U.S. Pat. No. 8,037,591 to Spivey discloses surgical scissors devices. The surgical scissors devices may comprise an end effector with first and second blade members. The first and second blade members may respectively comprise proximally positioned cams and distally positioned blade ends. Also, the first and second blade members may be coupled at a pivot point by a fastener held in tension along its longitudinal axis by the blade members. A reciprocating shuttle may comprise at least one pin positioned within slots defined by the respective cams of the blade members. Distally-directed motion of the shuttle may cause the first and second blade members to open and proximally-directed motion of the shuttle may cause the first and second blade members to close. Methods and apparatuses for forming the surgical scissors device are also disclosed Further, U.S. Pat. No. 6,562,035 to Levin discloses insulated surgical scissors having a cauterizing tip that permits a surgeon the ability to mechanically cut tissue that is purchased between the cutting blades of the scissors and to apply a cauterization current to a precise portion of the seized tissue, thereby minimizing inadvertent burning of surrounding tissue. Both monopolar and bipolar configurations of the insulated surgical scissors are provided.

Still further, U.S. Pat. No. 5,358,508 to Cobb discloses a laparoscopic instrument assembly having a removable tip attachable to an actuator, the actuator being provided with an actuator tube disposed for axial movement within a tubular sheath. The removable tip has a pair of blades forming a scissors which are moved between an open position and a closed position by axial movement of a tip tube disposed within a tubular tip casing structure. The tip tube is threaded to the actuator tube and the tip casing structure is threaded to the actuator tubular sheath, and a pair of thumb and finger grips serve to move the actuator tube within the tubular sheath.

However, these patents fail to provide a surgical instrument as defined in the present application. More specifically, these patents fail to define a surgical instrument which utilizes a liquid-tight heat-shrunk protective covering to cover the gap between the extended tube portion and the head portion of the surgical instrument. Further, these patents fail to provide a surgical instrument which utilizes a silicone or rubber seal at the gap (or 'interface') of the extended tube and the head portion to electrically insulate and protect the instrument all the way to the distal end of the surgical instrument.

SUMMARY OF THE INVENTION

A surgical instrument is provided, namely surgical scissors. The surgical instrument has liquid-tight heat-shrunk protective covering located at the business end of the surgical instrument which prevents contamination and damage to moving parts of the instrument which otherwise typically occurs between an extended tube portion of the surgical instrument and a head portion of the surgical instrument. Further, the liquid-tight heat-shrunk protective covering provides electrical insulation all the way to the distal tip of a clevis of the surgical instrument by use of a rubber (for example silicone) seal. The surgical instrument has a first blade and a second blade secured to the clevis. The first blade and second blade both have a triangular-shaped back end which allows the blades to fully extend and operate without the triangular-shaped back end of the first and second blade extending beyond the diameter of the clevis or tube of the surgical instrument.

An advantage of the present surgical instrument is that the present surgical instrument has a liquid-tight heat-shrunk protective covering which provides electrical insulation to the instrument all the way to the distal end of the surgical instrument.

Still another advantage of the present surgical instrument is that the entire head portion and tube portion of the present surgical instrument may be replaced while reusing the handle portion of the surgical instrument once the handle portion is sterilized.

Yet another advantage of the present surgical instrument is that the head portion of the present surgical instrument may have a clevis having a cam slot wherein the mechanical components of the head portion do not extend beyond the clevis of the head portion of the surgical instrument.

For a more complete understanding of the above listed features and advantages of the present surgical instrument, reference should be made to the following detailed description of the preferred embodiments and to the accompanying drawings.

BRIEF DESCRIPTION OF THE DRAWING

FIG. 1 illustrates a perspective view of the surgical instrument wherein a first blade and a second blade are in the Closed Position wherein the device has a liquid-tight heat-shrunk protective covering.

FIG. 2 illustrates a perspective view of the surgical instrument wherein the first blade and the second blade are in the Open Position wherein in the device has a liquid-tight heat-shrunk protective covering.

FIG. 3 illustrates a perspective view of the surgical instrument wherein the first blade and the second blade are in the Closed Position and wherein the liquid-tight heat-shrunk protective covering is removed.

FIG. 4 illustrates a perspective view of the surgical instrument wherein the first blade and the second blade are in the Open Position and wherein the liquid-tight heat-shrunk protective covering is removed.

FIG. 5 illustrates a close-up view of the head portion of the surgical instrument wherein the first blade and second blade are in the Closed Position with the clevis and the liquid-tight heat-shrunk protective covering removed.

FIG. 6 illustrates a close-up view of head portion of the surgical instrument wherein the first blade and the second blade are in the Open Position with the clevis and the liquid-tight heat-shrunk protective covering removed.

FIG. 7 illustrates a side view of the liquid-tight heat-shrunk protective covering on the surgical instrument and the blades of the instrument.

FIG. 8 illustrates a cross-sectional view of the liquid-tight heat-shrunk protective covering, the head portion and a portion of the extended rod portion of the surgical instrument.

FIG. 17 illustrates a perspective view of instrument installed into the cylindrical hollow tube.

FIG. 18 illustrates a cross sectional view of instrument when it is assembled into the hollow cylindrical tube.

DETAILED DESCRIPTION OF THE PREFERRED EMBODIMENTS

A surgical instrument is provided, namely surgical scissors. The surgical instrument has liquid-tight heat-shrunk protective covering located at the business end of the surgical instrument which prevents contamination and damage to moving parts of the instrument which otherwise typically occurs between an extended tube portion of the surgical instrument and a head portion of the surgical instrument. Further, the liquid-tight heat-shrunk protective covering provides electrical insulation all the way to the distal tip of a clevis of the surgical instrument by use of a rubber (for example silicone) seal. The surgical instrument has a first blade and a second blade secured to the clevis. The first blade and second blade both have a triangular-shaped back end which allows the blades to fully extend and operate without the triangular-shaped back end of the first and second blade extending beyond the diameter of the clevis or tube of the surgical instrument.

Figure 6A:
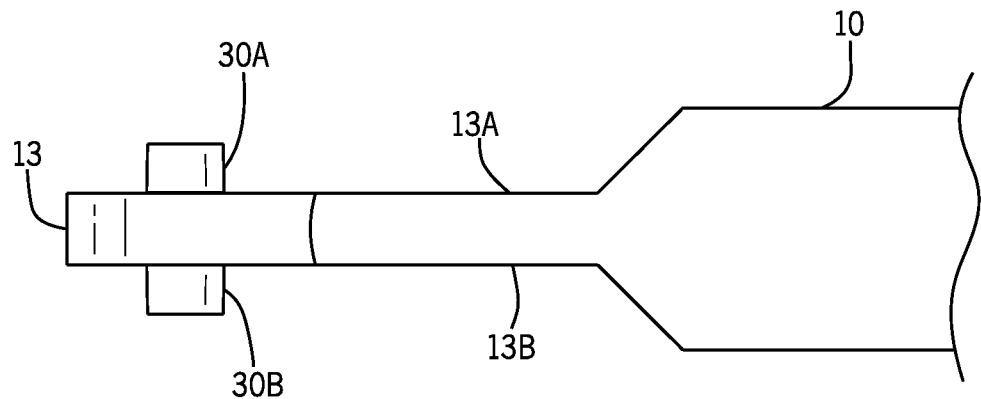
FIG. 6A illustrates a side view of the first end of the extended rod portion of the surgical instrument.
Figure 6B:
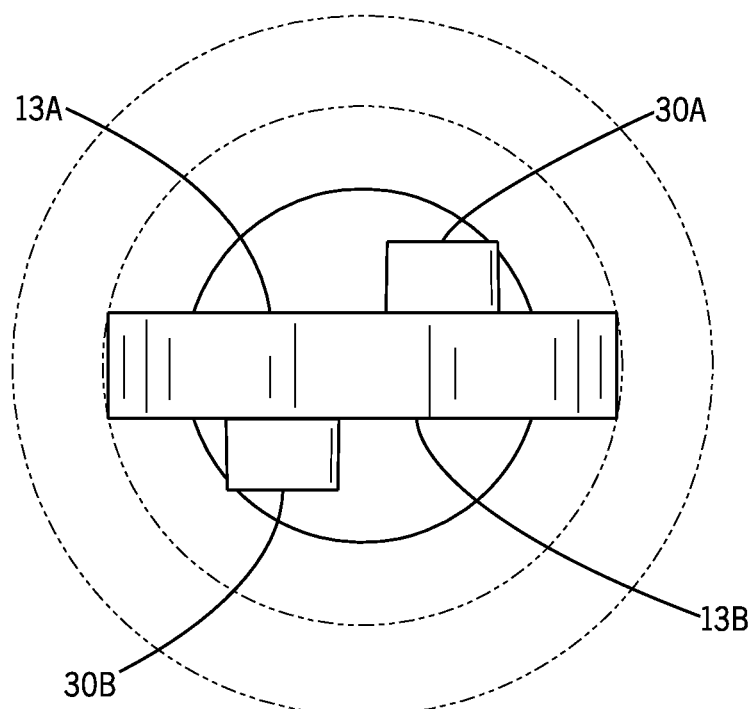
FIG. 6B illustrates a front view of the first end of the extended rod portion of the surgical instrument.
Figure 15:
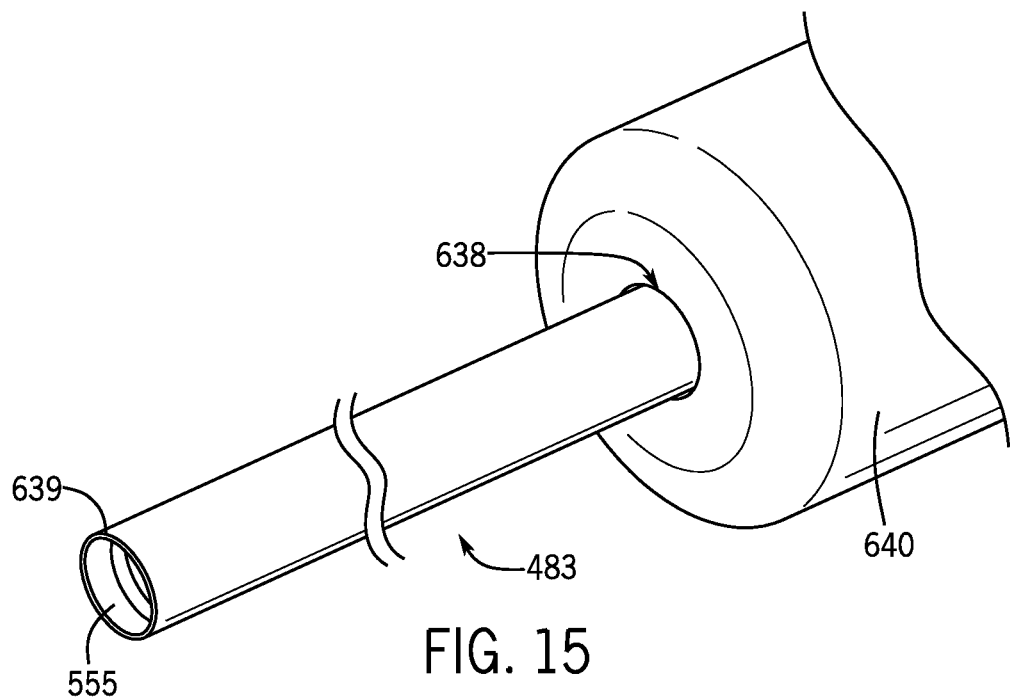
FIG. 15 illustrates the generally hollow cylindrical tube secured to the handle section.

Referring first to FIG. 1, in an embodiment, a surgical instrument 1 is provided. The surgical instrument 1 may have an extended rod portion 10, a head portion 50, a generally hollow cylindrical tube portion 483 which is non-conductive (FIG. 6), a generally conductive tube 484 (FIG. 16) which covers the extended rod portion 10 during use and a handle portion (partially illustrated as 640 in FIGS. 15 and 16). The surgical instrument 1 is preferably made predominately from a durable, non-corrosive metal, rubber and a liquid-tight heat-shrunk protective covering 100. In an embodiment, the rubber may be silicone.

Figure 9:
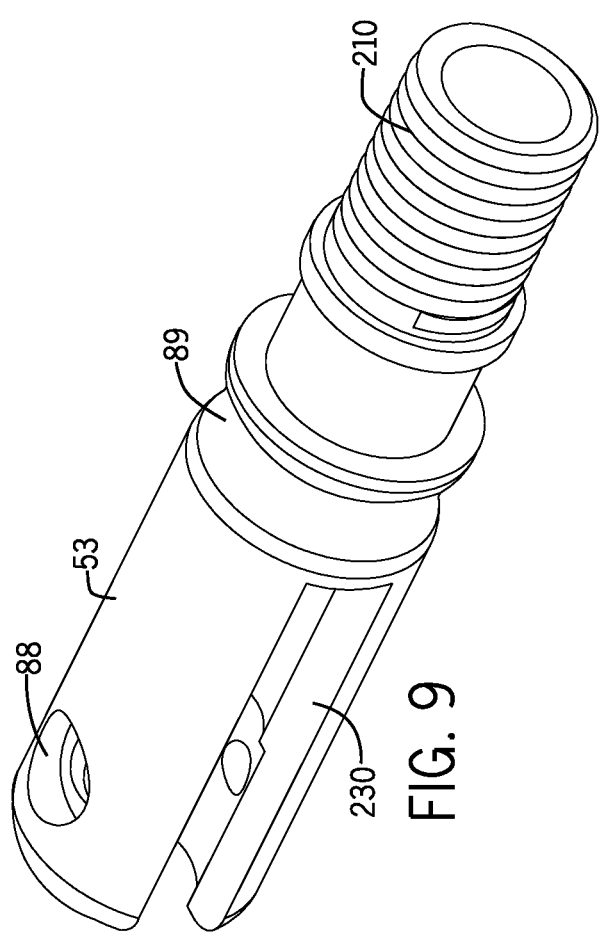
FIG. 9 illustrates a perspective view of the clevis unit of the surgical instrument with the blades removed.

Referring now to FIGS. 5 and 6, the head portion 50 may have a first end 51, a second end 52 and a clevis unit 53 (FIG. 9). The extended rod portion 10 may have a first end 11 (FIG. 8) and a second end 12 (FIG. 1). In an embodiment, the first end 11 of the extended rod portion 10 may be located at, and temporarily secured to, the head portion 50, as described below. The second end 12 of the extended rod portion 10 may be secured to and within the handle portion (not shown).

In an embodiment, the head portion 50 of the surgical instrument 1 may have a first blade 27 and a second blade 28. The first blade 27 may move with respect to the second blade 28. The first blade 27 and second blade 28 may be, for example, blades of scissors which may be used in performing a surgical procedure. In an embodiment, the first blade 27 may have a cam slot 27A and the second blade 28 may have a cam slot 28A. The cam slots 27A and 28A of the first blade 27 and second blade 28 may be generally rectangular in shape; each having an identical length 40 (FIG. 6).

In an embodiment, the first end 11 of the extended rod portion 10 may be secured within the clevis unit 53 of the head portion 50. Further, the clevis unit 53 may have a threaded portion 210 (FIG. 9) which correspondingly mates with and secures the generally hollow cylindrical tube portion 483 over the majority of the extend rod portion 10. More specifically, the generally hollow cylindrical tube portion 483 may have a first end 639 (FIG. 15) and a second end 638 wherein the first end 639 of the generally hollow cylindrical tube portion 483 is secured to the threaded portion 210 of the clevis unit 53 and wherein the second end 638 of the generally hollow cylindrical tube portion 483 is secured to the handle portion 640.

Figure 16:
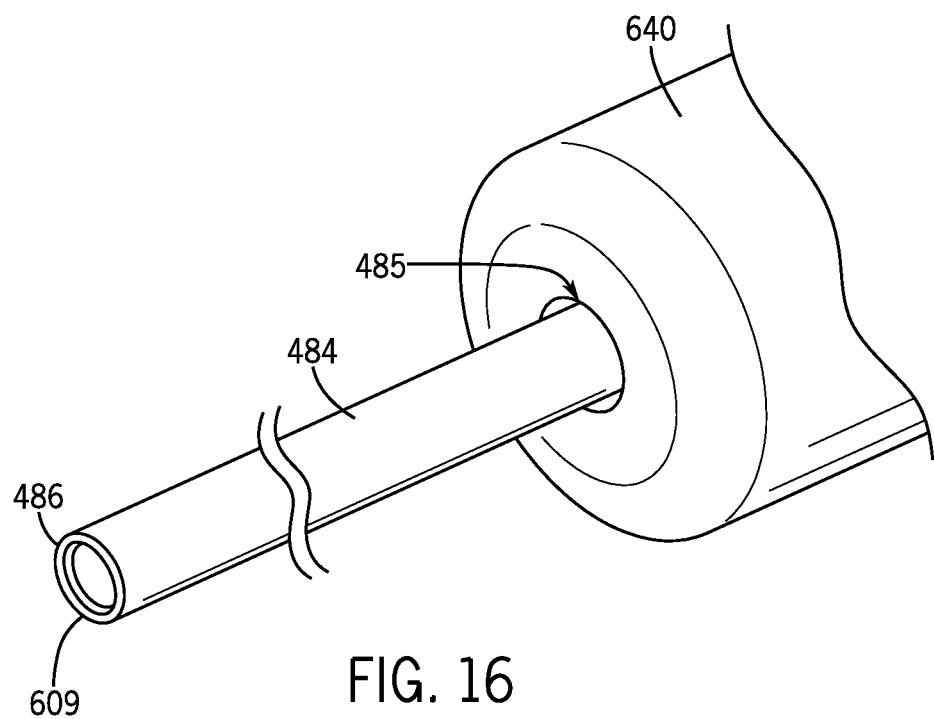
FIG. 16 illustrates the electrically conductive tube secured to the handle section.

As stated above, in an embodiment, the generally hollow cylindrical tube portion 483 may have a first end 639 and a second end 638. The second end 638 of the generally hollow cylindrical tube portion 483 may be connected to the instrument's handle 640 (partially shown in FIG. 15). Located within the interior of the generally hollow cylindrical tube portion 483 may be a generally conductive tube 484 (FIGS. 16 and 18). In particular, the generally cylindrical tube portion 483 may be electrically non-conductive (and thus insulating) whereas the generally conductive tube 484 located within the interior of the generally hollow cylindrical tube portion 483 is conductive. The generally conductive tube 484 may have a first end 485 and a second end 486 wherein the first end 485 is connected to the handle portion 640 and wherein the second end 486 is secured to the business end of the device 1. The generally conductive tube 484 may also have a female threaded portion 609 (FIG. 16) at the second end 486 which correspondingly mates with the threaded portion 210 of the clevis unit 53 of the surgical instrument 1. A hollow space 490 (FIG. 18) may surround the extended rod portion 10 and may be located between the extended rod portion 10 and the electrically conductive tube 484.

In an embodiment, the first end 11 of the extended rod portion 10 may be generally flat having an oval-shaped tip 13 (FIG. 8) having a top surface 13A (FIGS. 6A and 6B) and a bottom surface 13B. The top surface 13A of the oval-shaped tip 13 may have a drive pin 30A which extends in a perpendicular manner with respect to the generally flat first end 11 of the extended rod 10 and the bottom surface 13B of the oval-shaped tip 13 may have a drive pin 30B. In an embodiment, the drive pin 30A of the top surface 13A may be secured within the cam slot 27A and the drive pin 30B of the bottom surface 13B may be secured with the cam slot 28A of the blades 27, 28.

In an embodiment, the drive pin 30A of the top surface 13A may be off-set from the drive pin 30B of the bottom surface 13B so that the first blade 27 and second blade 28 may move from a Closed Position (FIG. 5) to an Open Position (FIG. 6) while requiring the least amount of movement of the second ends 91, 93 (described below) of the first blade 27 and second blade 28 within the clevis unit 53.

In an embodiment, the first blade 27 may have a first end 90 and a second end 91 (or "back end"). The second blade 28 may have a first end 92 and a second end 93 (or "back end"). The second end 91 of the first blade 27 and the second end 93 of the second blade 28 may generally be the second end 52 of the head portion 50. The second end 91 of the first blade 27 and the second end 93 of the second blade 28 may be generally triangular in shape; with the narrow tip portion of the triangle located away from the pivot pin 60 of the surgical instrument (as described below).

In an embodiment, the cam slot 27A of the first blade 27 may be located at one side of the "triangular" second end 91 of the first blade 27 while the cam slot 28A of the second blade 28 may be located on the opposing side of the "triangular" second end 93 of the second blade 28. The first blade 27 and the second blade 28 being separated by the first end 11 of the extended rod portion 10.

When the extended rod portion 10 is pushed forward with respect to the stationary generally hollow cylindrical tube portion 483 (by activating the handle), the drive pin 30A of the top surface 13A is moved forward within the cam slot 27A of the first blade 27 therein pivoting the first blade 27 (at the pivot pin 60) away from a main axis line 225 (FIG. 6) of the device 1. In addition, when the extended rod portion 10 is pushed forward, the second blade 28 also moves away from the main axis line 225, but in the opposing direction. To "cut" with the device 1, the handle is activated to pull the first blade 27 and second blade 28 back to the main axis line 225.

Because of the generally slim triangular shape of the second end 91 of the first blade 27 and the generally slim triangular shape of the second end 93 of the second blade 28, both second ends 91, 93 do not extend beyond a length 285 as defined by the diameter 285 of the generally hollow cylindrical tube portion 483 (and clevis unit 53). As a result, both second ends 91, 93 permanently remain beneath the liquid-tight heat-shrunk protective covering 100 of the surgical instrument 1 and completely within the clevis unit 53 during use.

Figure 10:
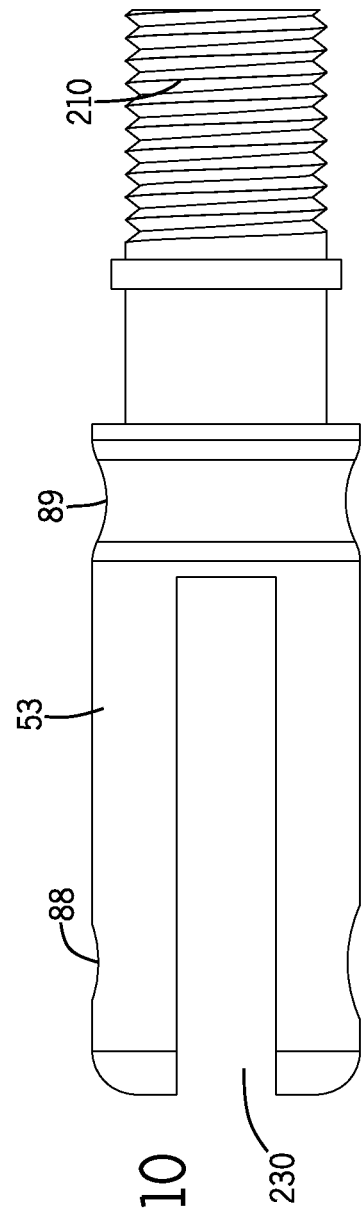
FIG. 10 illustrates a side view of the clevis unit of the surgical instrument with the blades removed.
Figure 13:
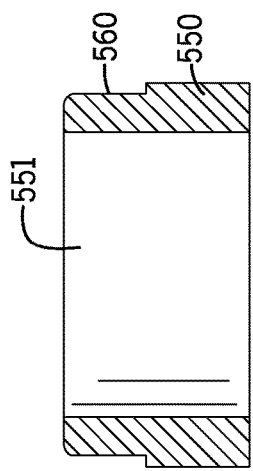
FIG. 13 illustrates a cross-sectional view of the rubber seal of the surgical instrument.
Figure 12:
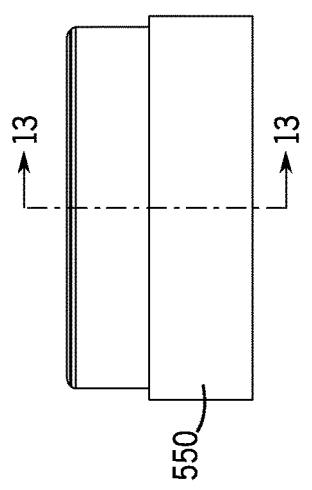
FIG. 12 illustrates a side view of the rubber seal of the surgical instrument.
Figure 14:
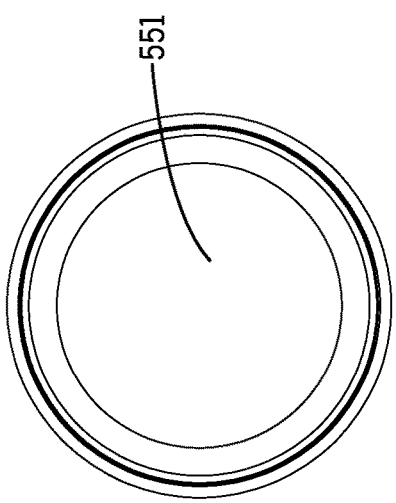
FIG. 14 illustrates a top view of the rubber seal of the surgical instrument.
Figure 11:
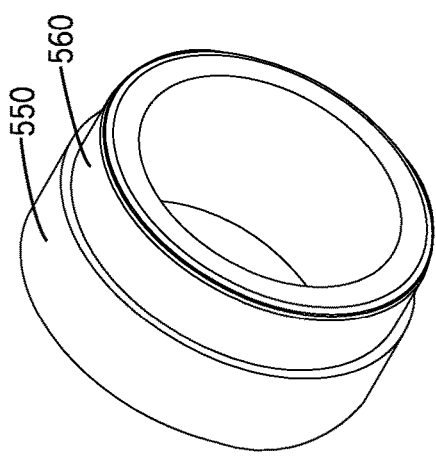
FIG. 11 illustrates a perspective view of the rubber (for example, silicone) seal of the surgical instrument.

As stated above, in an embodiment, the head portion 50 may have a pivot pin 60 which may extend through both the first blade 27 and the second blade 28. In particular, the pivot pin 60 of the head portion 50 may extend partially through an opening 88 (FIG. 9) in the clevis unit 53 which secures the pivot pin 60. The pivot pin 60 may connect the first blade 27 to the second blade 28 and may be the rotational axis point with respect to the first blade 27 to the second blade 28. In an embodiment, the clevis unit 53 may have an extended slot 230 (FIGS. 9 and 10). The extended slot 230 may allow the first blade 27 and the second blade 28 to pivot from the First Position to the Second Position.

Referring again to FIG. 8, in an embodiment, a liquid-tight heat-shrunk protective covering 100 may be secured over a portion of the surgical instrument 1. In particular, the liquid-tight heat-shrunk protective covering 100 may have a first end 101 and a second end 102. The liquid-tight heat-shrunk protective covering 100 may be secured over the head portion 50 of the instrument 1 extending to the generally hollow cylindrical tube portion 483 of the instrument 1. In an embodiment, the liquid-tight heat-shrunk protective covering 100 may be generally cylindrical, having an indentation portion 110. The indentation portion 110 may allow the liquid-tight heat-shrunk protective covering 100 to properly and securely grasp the surgical instrument 1 (as described below).

The generally hollow cylindrical tube portion 483 may be made from the same material as the liquid-tight heat-shrunk protective covering 100. In an embodiment, the generally hollow cylindrical tube portion 483 may be thicker than the liquid-tight heat-shrunk protective covering 100. The compression of the generally cylindrical seal 550 (which is rubber and preferably silicone) caused by a portion of the interior surface of the first end 639 of the hollow cylindrical tube portion 483 and the protective covering 100, prevents the electricity from passing from the extended rod portion 10, the clevis unit 53, the back ends of blades 27, 28, and/or the conductive hollow tube 484 to the main exterior portion (IE—generally cylindrical tube portion 483) of the device 1 and/or to the protective covering 100 at the head of the device 1. More specifically, in prior art devices, a large portion of the exterior of the surgical instrument becomes accidentally electrically active as a result of the interior (and intended) metal portions of the device occasionally contacting the exterior covering without a proper seal to insulate the device.

The generally cylindrical seal 550 forms an electrical barrier at the interface of the generally hollow cylindrical tube portion 483 and the clevis unit 53 when the device 1 is fully assembled which therein allows the device 1 to be fully insulated from the second end 638 of the generally hollow cylindrical tube portion 483 to the first end 101 of the liquid-tight heat-shrunk protective covering 100. This prevents any electrical energy from exiting radially from the device 1 between second end 638 of the generally hollow cylindrical tube portion 483 to end 101 of the liquid-tight heat-shrunk protective covering 100. All electrical energy is then directed out of the intended region of the instrument; IE the front of the blades 27 and 28. Referring to FIG. 18, in an embodiment, the generally cylindrical seal 550 is partially covered by the generally hollow cylindrical tube portion 483 and partially covered by the liquid-tight heat-shrunk protective covering 100.

In an embodiment, the liquid-tight heat-shrunk protective covering 100 may cover the clevis unit 53 of the device 1 so that the clevis unit 53 is protected from damage. Because the first blade 27 and the second blade 28 of the clevis unit 53 operate the scissors without the first blade 27 or the second blade 28 extending beyond the circumference (or diameter 285) of the extended rod portion 10, the scissors may fully operate while the second end 52 of the head portion 50 remain completely secured with the liquid-tight heat-shrunk protective covering 100.

Referring now to FIGS. 9 and 10, in an embodiment, the clevis unit 53 may have an indentation portion 89 wherein the indentation portion 89 has a smaller circumference then the rest of the main body of clevis unit 53. The indentation portion 89 of the clevis unit 53 may be located below the indentation portion 110 of the liquid-tight heat-shrunk protective covering 100 and may help secure the liquid-tight heat-shrunk protective covering 100 to the clevis unit 53. More specifically, it may be more difficult for the liquid-tight heat-shrunk protective covering 100 to accidentally shift with respect to the clevis unit 53 as a result of the indentation portion 110 of the liquid-tight heat-shrunk protective covering 100 locking into and grasping the indentation portion 89 of the clevis unit 53.

Referring now to FIGS. 11-14, in an embodiment, the surgical instrument 1 may have a generally cylindrical seal 550. The generally cylindrical seal 550 may have an opening 551 for receiving a portion of the clevis unit 53 and a portion of the extended rod portion 10. The generally cylindrical seal 550 may have a portion 560 having a thinner circumference. The generally cylindrical seal 550 may surround a portion of the clevis unit 53 (FIG. 8). In an embodiment, the liquid-tight heat-shrunk protective covering 100 may partially grasp and cover a portion of the generally cylindrical seal 550 so as to more securely cover and protect the business end of the surgical instrument 1.

Further, in an embodiment, the liquid-tight heat-shrunk protective covering 100 and the generally cylindrical seal 550 together may allow the surgical instrument to be electrically insulated (on the exterior of the device 1) all the way from the blades 27, 28 to and including the handle portion 640 of the instrument. As a result, the exterior of the device 1 is insulated from the blades 27, 28 to and including the handle portion 640 while the interior of the device 1 (including the extended rod 10, the generally conductive tube 484, the clevis unit 53, etc) of the device 1 is largely electrically conductive.

The electrical insulation is provided as a result of the generally cylindrical seal 550 being rubber and being compressed at the first end 639 of the generally hollow cylindrical tube portion 483 by a portion 555 (FIG. 15) of the interior of the generally hollow cylindrical tube 483. The compression (illustrated at 570 of FIG. 18 by arrows) is a result of the thinner portion 560 of the generally cylindrical seal 550 having a slightly greater circumference than the inner portion 555 of the first end 639 of the generally hollow cylindrical tube portion 483. Further, the distal end 491 of the electrically conductive tube 484 may contact the end of the generally conductive seal 550.

The liquid-tight heat-shrunk protective covering 100 may be applied partially over and may grasp a portion of the generally cylindrical seal 550 (See FIG. 8). As stated above, this may cause a region of electrical insulation to form from the generally cylindrical seal 550 to the second end 102 of the liquid-tight heat-shrunk protective covering 100. As a result, the generally cylindrical seal 550 may allow some of the interior components of the instrument 1, specifically, the clevis unit 53, the first end 11 of the extended rod portion 10 and the blades 27, 28 to remain electrically conductive while still providing electrical insulation on the exterior surface of the instrument 1 from the second end 102 of the liquid-tight heat-shrunk protective covering 100 to the first end 101 of the liquid-tight heat-shrunk protective covering 100.

Although embodiments of the present invention are shown and described therein, it should be understood that various changes and modifications to the presently preferred embodiments will be apparent to those skilled in the art. Such changes and modifications may be made without departing from the spirit and scope of the present invention and without diminishing its attendant advantages. It is, therefore, intended that such changes and modifications be covered by the present application.

The invention claimed is:

1. A surgical instrument comprising:
   a handle portion;
   a cylindrical hollow tube secured to the handle portion the cylindrical hollow tube having a first end and a second end wherein the second end of the cylindrical hollow tube is secured to the handle portion;
   a clevis unit secured within a cylindrical covering wherein the cylindrical covering has a first end and a second end and wherein second end of the cylindrical covering is located adjacent to the first end of the cylindrical hollow tube;
   a first blade and a second blade wherein a portion of the first blade and a portion of the second blade are secured within the clevis unit;
   a rubber seal partially covered by the first end of the cylindrical hollow tube and partially covered by the second end of the cylindrical covering;
   a first end of the first blade and a second end of the first blade;
   a first end of the second blade and a second end of the second blade; and
   wherein the second end of the first blade and the second end of the second blade do not extend outside of a circumference of the clevis unit at any time, while the first end of the first blade and the first end of the second blade extend outside of the circumference of the clevis unit.

2. The surgical instrument of claim 1 wherein the cylindrical covering is heat-shrunk over the clevis unit.

3. The surgical instrument of claim 1 wherein the rubber seal is silicone.

4. The surgical instrument of claim 1 wherein the first blade and the second blade are electrically conductive and have an electrical charge and wherein the rubber seal prevents the electrical charge from passing from the first blade or second blade to the cylindrical hollow tube.

5. The surgical instrument of claim 1 further comprising:
   a second hollow tube wherein the second hollow tube is located within an interior of the cylindrical hollow tube and therein the second hollow tube surrounds an extended rod of the surgical instrument and wherein the extended rod and the second hollow tube are electrically conductive and have an electrical charge.

6. The surgical instrument of claim 5 wherein the cylindrical hollow tube is heat-shrunk over the second hollow tube.

7. The surgical instrument of claim 1 wherein the cylindrical hollow tube is electrically non-conductive.

8. The surgical instrument of claim 1 wherein the cylindrical covering is electrically non-conductive.

9. The surgical instrument of claim 1 wherein the clevis unit is electrically conductive.

10. The surgical instrument of claim 1 further comprising:
    a cylindrical indentation on the cylindrical covering having a reduced circumference wherein the cylindrical indentation of the cylindrical covering correspondingly matches with and mates with a cylindrical indentation of the clevis unit wherein the cylindrical indentation of the clevis unit has a reduced circumference and wherein the corresponding cylindrical indentation of the cylindrical covering and the cylindrical indentation of the clevis unit together secure the cylindrical covering onto the clevis unit.

11. The surgical instrument of claim 5 further comprising:
    a generally flat portion of the extended rod wherein the generally flat portion has a first side and a second side;
    a first pin secured on the first side of the generally flat portion and a second pin secured on the second side of the generally flat portion wherein the first pin and the second pin each are received in a separate cam slot located on the first blade and the second blade.

12. The surgical instrument of claim 5 further comprising:
    a threaded portion of the clevis unit wherein the threaded portion of the clevis unit mates with a corresponding threaded portion of the second hollow tube.

13. The surgical instrument of claim 5 wherein the cylindrical covering of the clevis unit and the cylindrical hollow tube both remain electrically non-conductive while the first blade, the second blade, the extended rod and the second cylindrical tube remain electrically conductive.

14. The surgical instrument of claim 1 wherein the rubber seal has a first circumference and a second circumference wherein the first circumference is greater than the second circumference.

15. The surgical instrument of claim 14 wherein the second circumference of the rubber seal is slightly compressed by a portion of the cylindrical hollow tube.

16. A surgical instrument comprising:
a handle portion;
a cylindrical hollow tube secured to the handle portion the cylindrical hollow tube having a first end and a second end wherein the second end of the cylindrical hollow tube is secured to the handle portion;
a clevis unit secured within a cylindrical covering wherein the cylindrical covering has a first end and a second end and wherein second end of the cylindrical covering is located adjacent to the first end of the cylindrical hollow tube;
a first blade and a second blade wherein a portion of the first blade and a portion of the second blade are secured within the clevis unit;
a rubber seal partially covered by the first end of the cylindrical hollow tube and partially covered by the second end of the cylindrical covering; and
a cylindrical indentation on the cylindrical covering having a reduced circumference wherein the cylindrical indentation of the cylindrical covering correspondingly matches with and mates with a cylindrical indentation of the clevis unit wherein the cylindrical indentation of the clevis unit has a reduced circumference and wherein the corresponding cylindrical indentation of the cylindrical covering and the cylindrical indentation of the clevis unit together secure the cylindrical covering onto the clevis unit.

17. A surgical instrument comprising:
a handle portion;
a cylindrical hollow tube secured to the handle portion the cylindrical hollow tube having a first end and a second end wherein the second end of the cylindrical hollow tube is secured to the handle portion;
a clevis unit secured within a cylindrical covering wherein the cylindrical covering has a first end and a second end and wherein second end of the cylindrical covering is located adjacent to the first end of the cylindrical hollow tube;
a first blade and a second blade wherein a portion of the first blade and a portion of the second blade are secured within the clevis unit;
a rubber seal partially covered by the first end of the cylindrical hollow tube and partially covered by the second end of the cylindrical covering;
a second hollow tube wherein the second hollow tube is located within an interior of the cylindrical hollow tube and therein the second hollow tube surrounds an extended rod of the surgical instrument and wherein the extended rod and the second hollow tube are electrically conductive and have an electrical charge; and
a generally flat portion of the extended rod wherein the generally flat portion has a first side and a second side;
a first pin secured on the first side of the generally flat portion and a second pin secured on the second side of the generally flat portion wherein the first pin and the second pin each are received in a separate cam slot located on the first blade and the second blade.

* * * * *